US00PP20695P2

(12) United States Plant Patent
Wright et al.

(10) Patent No.: US PP20,695 P2
(45) Date of Patent: Feb. 2, 2010

(54) BLUEBERRY PLANT NAMED 'C99-42'

(50) Latin Name: ***Vaccinium* hybrid**
Varietal Denomination: C99-42

(75) Inventors: Gary Wright, Corindi Beach (AU); Paul Lyrene, Micanopy, FL (US)

(73) Assignee: Costaexchange Limited, New South Wales (AU)

( * ) Notice: Subject to any disclaimer, the term of this patent is extended or adjusted under 35 U.S.C. 154(b) by 0 days.

(21) Appl. No.: 12/228,525

(22) Filed: Aug. 12, 2008

(51) Int. Cl.
*A01H 5/00* (2006.01)

(52) U.S. Cl. ..... Plt./157
(58) Field of Classification Search ..... Plt./157
See application file for complete search history.

*Primary Examiner*—Annette H Para
(74) *Attorney, Agent, or Firm*—Ballew Law

(57) ABSTRACT

A new and distinct cultivar of blueberry (*Vaccinium* hybrid) plant named 'C99-42', characterized by its combination of spreading plant shape and strong plant growth vigor, evergreen foliage, early to mid-season of flowering and fruiting, medium fruit size, very firm fruit suited to handling, attractive dark blue fruit color and small picking scar. This combination results in higher quality fruit with an earlier availability than other varieties.

3 Drawing Sheets

Latin name of genus and species of plant claimed: *Vaccinium* hybrid.

Variety denomination: 'C99-42'.

BACKGROUND OF THE INVENTION

The present invention relates to a new and distinct perennial variety of *Vaccinium* hybrid (Southern Highbush Blueberry), which has been given the variety denomination of 'C99-42'. Its market class is that of a fruiting plant. 'C99-42' is intended for use as fresh fruit for shipping, customer pick and processing markets and as a home garden plant.

The new blueberry cultivar is a selection resulting from seedlings produced in a controlled breeding programme of *Vaccinium* at Gainesville, Fla., USA in 1996 from a cross of seed parent 'F97-47' (unpatented) and pollen parent 'F 88-53' (patented as 'Windsor' U.S. Plant Pat. No. 12,783). The new cultivar was discovered and selected as a single plant within a population of blueberry plants in 1999 in a commercial field plantation environment at Corindi Beach, New South Wales, Australia. Selection criteria was a combination of upright to bushy plant shape and strong plant growth vigor, evergreen foliage, earliness of flowering and fruiting, large fruit size, firm fruit suited to handling, attractive dark blue fruit color and small picking scar. The selection was subsequently evaluated for a number of years at the commercial farms of BerryExchange at Corindi Beach, New South Wales, Australia.

Asexual reproduction of the new cultivar by cutting propagation since 1999 at Corindi Beach, New South Wales, Australia and has demonstrated that the new cultivar reproduces true to type with all of the characteristics, as herein described, firmly fixed and retained through successive generations of such asexual propagation.

The new variety has been primarily compared to the variety 'Sharpe Blue' (unpatented). In Corindi Beach, New South Wales, Australia the time of fruit ripening of 'C99-42' is classified as 'early to mid-season' whereas the time of fruit ripening of 'Sharpe Blue' is classified as 'mid-season'. The earlier time of fruit ripening of 'C99-42' allows for a greater period of production on farm and an ability to supply fresh fruit markets at an earlier date than 'Sharpe Blue'. The time of vegetative bud burst of 'C99-42' is 'medium to late' whereas the time of vegetative bud burst of 'Sharpe Blue' is 'early to mid-season'. The time of beginning of flowering of 'C99-42' is classified as 'early to mid-season' which is similar to the time of beginning of flowering of 'Sharpe Blue'. The time of fruit ripening of 'C99-42' is classified as 'early to mid-season' whereas 'Sharpe Blue' is classified as 'mid-season'. Therefore one of the attributes of the new variety is that it has vegetative bud burst later than 'Sharpe Blue', yet its fruit ripens earlier than 'Sharpe Blue'. The plant growth habit of 'C99-42' is 'spreading' whereas the plant growth habit of 'Sharpe Blue' is 'bushy to spreading'. The leaf width of 'C99-42' is 'narrow' (20–25 mm) whereas the leaf width of 'Sharpe Blue' is 'broad' (40–45 mm). The berry color of 'C99-42' is a dark blue whereas the berry color of 'Sharpe Blue' is a lighter blue. The berry firmness of 'C99-42' is firm whereas 'Sharpe Blue' is soft. The picking scar of 'C99-42' is classified as 'dry' whereas the picking scar of 'Sharpe Blue' is 'wet'. This combination of fruiting attributes results in 'C99-42' being a more suitable variety for commercial handling including picking and packing than 'Sharpe Blue'.

SUMMARY OF THE INVENTION

The following characteristics of the new cultivar have been repeatedly observed and can be used to distinguish 'C99-42' as a new and distinct cultivar of blueberry plant:

1. Spreading plant growth habit
2. Mid-season to late timing of vegetative bud burst
3. Early to mid-season timing of beginning of flowering
4. Early to mid-season timing of fruit ripening
5. Dark blue berry color
6. Berry firmness is firm to very firm
7. Picking scar is dry Plants of the new cultivar differ from plants of the parents primarily in spreading growth habit, medium fruit size, dark blue colour and dry picking scar, whereas the parent varieties have a bushy to semi-spreading growth habit, very large fruit size, light blue colour and medium to wet picking scar.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'C99-42'.

DETAILED BOTANICAL DESCRIPTION

Figure 1:
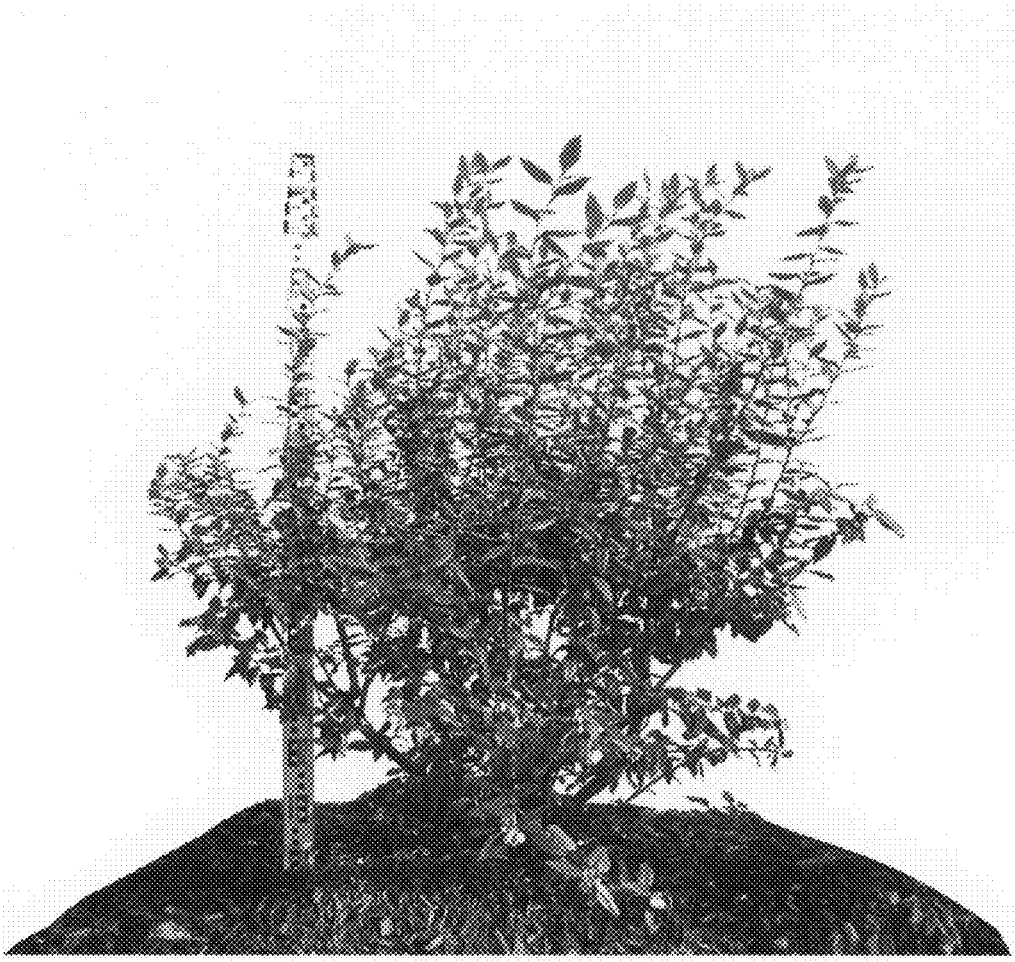
FIG. 1 illustrates a 'C99-42' plant in a commercial field planting.
Figure 2:
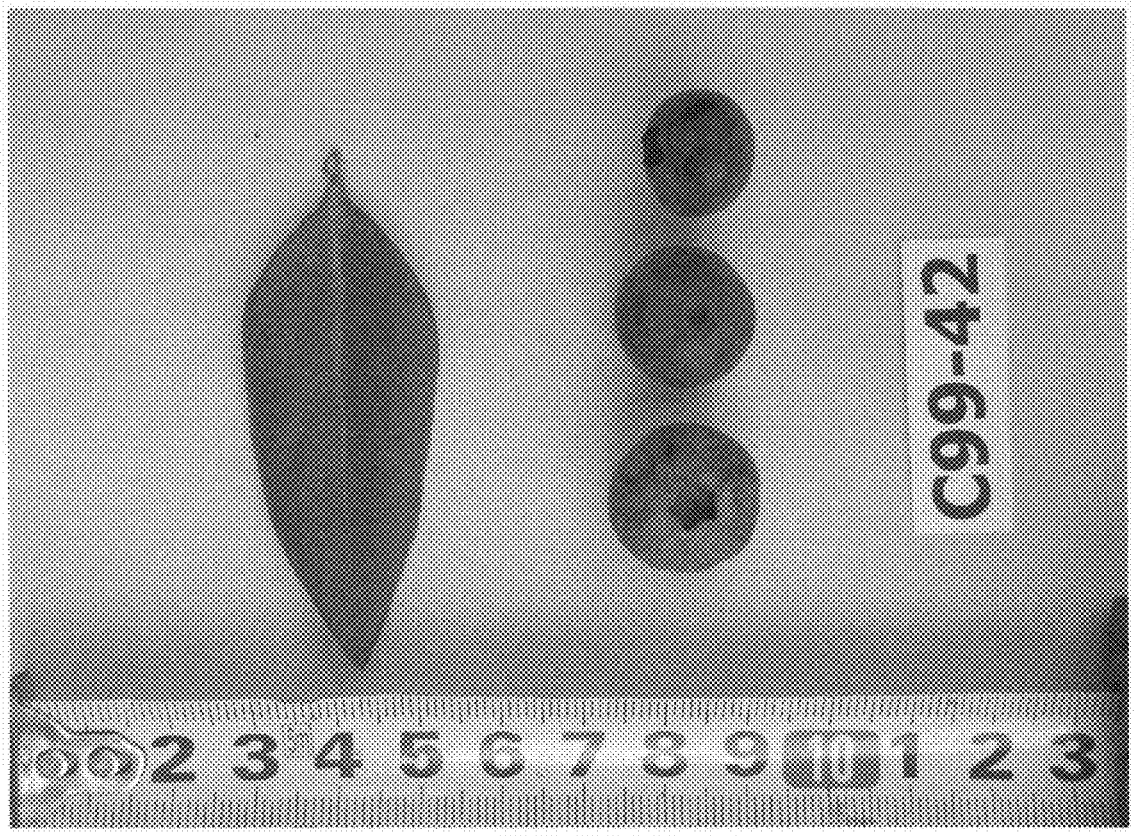
FIG. 2 illustrates 'C99-42' leaf and berry shapes and dimensions.
Figure 3:
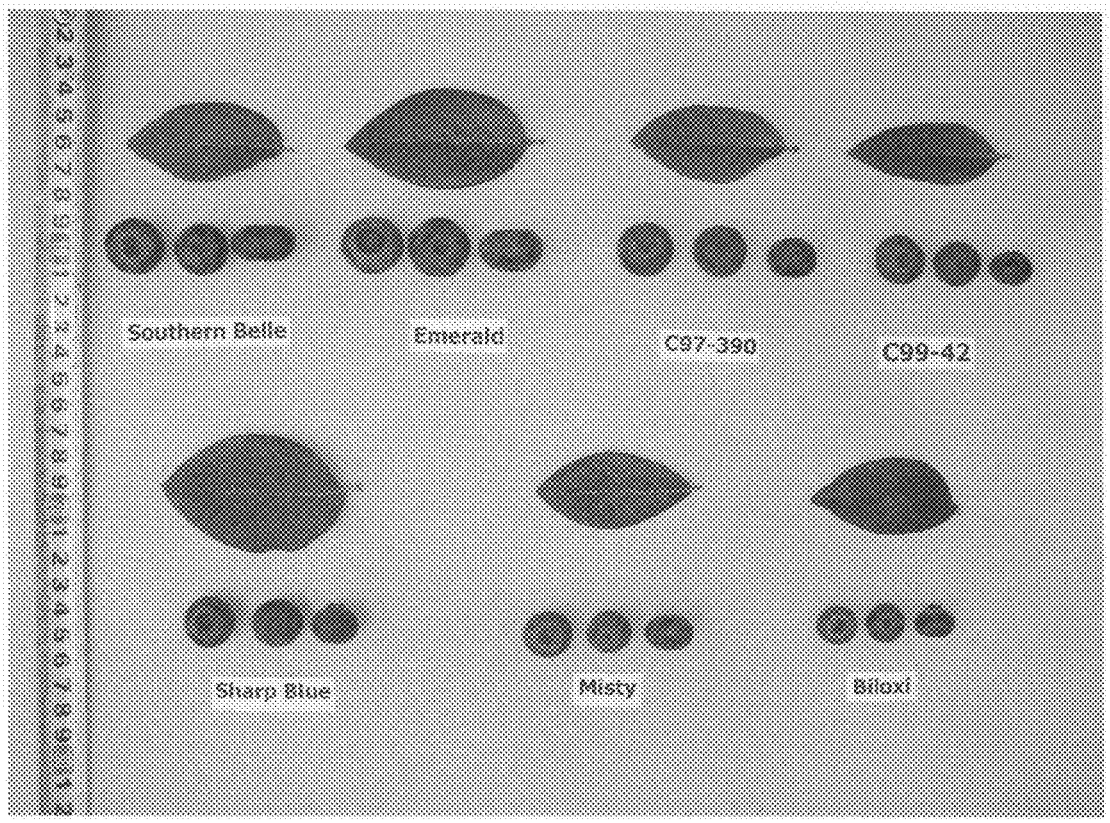
FIG. 3 illustrates 'C99-42' leaf and berry shapes and dimensions compared to other commercial cultivars.

The following is a detailed botanical description of a new and distinct variety of a *Vaccinium* hybrid ornamental plant known as 'C99-42'. Plant observations were made on plants grown in Corindi Beach, New South Wales, Australia. Unless indicated otherwise, the descriptions disclosed herein are based upon observations made from August to September 2007 of mature 'C99-42' plants (age 4 years) grown in outdoor field plantings with day temperature ranging from 21° C. to 23° C., night temperatures ranging from 10° C. to 12° C., and light levels ranging from 6 to 8 klux. Those skilled in the art will appreciate that certain characteristics will vary with older or, conversely, younger plants. 'C99-42' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 1995 edition.

Botanical classification: *Vaccinium* hybrid cultivar C99-42.

Parentage:

*Parents.*—Seed parent 'F97-47' (unpatented) and pollen parent 'F88-53' (patented as 'Windsor' PP12,783).

Plant:

*Growth habit.*—Plants are spreading. Growth vigor is strong. Plant height is 1.6 m. Plant width is 1.5 m. Flower bud density is medium. Twigginess is high. Time of beginning of leaf bud burst is medium to late (mid to early September) when grown as an evergreen in Australia. Time of beginning of flowering is early to mid-season (begins mid May; peaks mid August) when grown as an evergreen in Australia. Time of fruit ripening is early to mid-season (begins mid July; peaks late September to early October) when grown as an evergreen in Australia Stem:

*Suckering tendency.*—Plants typically have 5–7 major canes per plant from a base 30 cm in diameter on 6 year old plants.

*Canes.*—Erect to semi-erect with moderate branching; color greyed orange 198C; 2 year old cane diameter 12 mm, colored greyed orange 177B, some flaking of bark, current season wood diameter 3–4 mm, colored yellow green 144C Internode length on strong, new shoots: 15–20 mm.

*Fruiting wood.*—Numerous twigs to 10 cm in length.

*Surface texture of new wood.*—Smooth.

Fully developed leaf:

*Length.*—Medium 60–70 mm.

*Width.*—Medium approximately 22–26 mm.

*Shape.*—Elliptic.

*Color.*—Yellow green 137A.

*Intensity of color.*—Medium.

*Margin.*—Entire.

*Undulation of margin.*—Weak.

*Pubescence of upper side.*—Absent.

*Pubescence of lower side.*—Absent.

*Cross sectional profile.*—Flat.

*Longitudinal profile.*—Straight.

*Attitude.*—Broad acute to horizontal.

Inflorescence:

*Length of peduncle.*—To 12 mm.

*Length of pedicel.*—Long 4–5 mm.

*Number of flowers per cluster.*—Median 7.

*Flower cluster density is.*—Medium.

Flowers:

*Length of corolla tube.*—Short-medium (to 13 mm).

*Width of corolla tube.*—Narrow-medium (to 9 mm).

*Corolla aperture diameter.*—3 mm.

*Color of corolla.*—White 155D.

*Anthocyanin coloration of corolla.*—Absent.

*Corolla.*—Ridges present.

*Protrusion of stigma.*—Absent.

*Fragrance.*—Weak.

*Shape.*—Urceolate.

*Abundance of pollen.*—High.

*Calyx* (*with sepals*).—Diameter 5–6 mm.

*Calyx color,*—Green 138A.

Productivity: 3 to 4 kg per season from 3–4 year old plants planted at 3.0 m ×0.9 m density.

Cold hardiness: C99-42 has not been grown in all environments including harsh winter environments. Cold tolerance is expected to be low.

Chilling requirement: C99-42 has not been grown in all environments and is typically grown as an evergreen crop where chilling hours are not important. C99-42 is classed as 'low chill', typical of Southern Highbush Blueberry varieties with an estimated chilling requirement of 350 hours (not tested).

Leafing: Plants retain leaves year round (at Corindi beach, NSW Australia) and C99-42 is grown commercially as an evergreen crop. New leafing occurs in mid to early September at Corindi beach, NSW Australia.

Fruit:

*Unripe fruit color intensity.*—Light.

*Unripe fruit color,*—144A.

*Cluster density is.*—Medium.

*Diameter is.*—Medium (mean 17.5 mm).

*Weight.*—Medium (approximately 2.3 g).

*Shape.*—Globose.

*Attitude of calyx.*—Erect.

*Diameter of calyx basin.*—Medium (mean 6.5 mm).
*Depth of calyx basin is.*—Shallow (to 1 mm).
*Intensity of bloom.*—Medium to strong.
*Intensity of blue color of skin with bloom removed is.*—Very dark.
*Color of skin.*—202A.
*Sweetness when ripe.*—Strong.
*Firmness when ripe.*—Firm to very firm.
*Acidity when ripe.*—Weak.
*Size of scar is.*—Small (1.0–1.5 mm).
*Storage quality.*—Good.

Date of 50% maturity: Approximately 25$^{th}$ September at Corindi beach, NSW Australia.

Fruit development period: Approximately 60 days in protected cultivation at Corindi beach, NSW Australia.

Speed:
*Seed color.*—Greyed orange 165B.
*Seed abundance in fruit.*—Medium.
*Seed size.*—1.6–1.8 mm long for fully developed seeds.

Tolerance to disease: C99-42 has shown good resistance to root disease (*phytophthora* spp) and medium to good resistance to blueberry rust compared to commercial varieties 'Sharpe Blue' and 'Emerald'. Also demonstrates good resistance to the fruit disease Anthracnose (*Colletotrichum gleosporoides*).

What is claimed is:

1. A new and distinct cultivar of blueberry plant named 'C99-42', substantially as herein shown and described.

* * * * *